US006482440B2

(12) United States Patent
Zemlan et al.

(10) Patent No.: US 6,482,440 B2
(45) Date of Patent: Nov. 19, 2002

(54) LONG ACTING ANTIDEPRESSANT MICROPARTICLES

(75) Inventors: Frank P. Zemlan, Cincinnati, OH (US); Jeffrey Mulchahey, Hamilton, OH (US)

(73) Assignee: Phase 2 Discovery, Inc., Cincinnati, OH (US)

( * ) Notice: Subject to any disclaimer, the term of this patent is extended or adjusted under 35 U.S.C. 154(b) by 0 days.

(21) Appl. No.: 09/943,184

(22) Filed: Aug. 30, 2001

(65) Prior Publication Data

US 2002/0132854 A1 Sep. 19, 2002

Related U.S. Application Data

(60) Provisional application No. 60/234,434, filed on Sep. 21, 2000.

(51) Int. Cl.$^7$ .............................................. A16K 31/27
(52) U.S. Cl. ...................................... 424/489; 424/401
(58) Field of Search ................................. 424/400, 489

(56) References Cited

U.S. PATENT DOCUMENTS

| | | | |
|---|---|---|---|
| 4,029,731 A | 6/1977 | Sarges | 424/316 |
| 4,045,488 A | 8/1977 | Sarges | 260/576 |
| 4,389,330 A | 6/1983 | Tice et al. | 427/213.36 |
| 4,536,518 A | 8/1985 | Welch, Jr. et al. | 514/647 |
| 4,556,676 A | 12/1985 | Welch, Jr. et al. | 514/554 |
| 5,178,878 A | 1/1993 | Wehling et al. | 424/460 |
| 5,622,657 A * | 4/1997 | Takada et al. | 264/4.32 |
| 5,650,173 A | 7/1997 | Ramstack et al. | 424/489 |
| 5,651,990 A | 7/1997 | Takada et al. | 424/497 |
| 5,654,008 A | 8/1997 | Herbert et al. | 424/489 |
| 5,723,269 A | 3/1998 | Akagi et al. | 424/497 |
| 5,770,231 A | 6/1998 | Mesens et al. | 424/497 |
| 5,955,459 A | 9/1999 | Bradley et al. | 514/220 |
| 6,022,562 A | 2/2000 | Autant et al. | 424/489 |
| 6,342,496 B1 * | 1/2001 | Jerussi et al. | 514/231.2 |

OTHER PUBLICATIONS

Markowitz, et al., Treating Depression in HIV–Positive Patients, AIDS, 8: 403–412 (1994).

Demyttenaere, "Compliance During Treatment with Antidepressants," Journal of Affective Disorders 43: 27–39 (1997).

* cited by examiner

Primary Examiner—Jose' G. Dees
Assistant Examiner—Konata M. George
(74) Attorney, Agent, or Firm—Frost Brown Todd LLC

(57) ABSTRACT

Pharmaceutically-active materials comprising specific antidepressant compounds, such as sertraline, contained in microparticles formulated so as to release the antidepressant compounds over an extended period of time are disclosed. The materials, when administered, particularly by injection, release the active agent over time allowing the patient to be effectively treated without requiring multiple dosing of the pharmaceutical material. Pharmaceutical compositions containing the microparticles and methods of treating depression-related conditions utilizing the microparticles are also disclosed.

17 Claims, No Drawings

LONG ACTING ANTIDEPRESSANT MICROPARTICLES

This application is based on and claims priority from U.S. Provisional Application Serial No. 60/234,434, filed Sep. 21, 2000.

TECHNICAL FIELD

The present invention relates to pharmaceutically-active compositions, particularly injectable compositions, which provide long-acting antidepressant activity.

BACKGROUND OF THE INVENTION

Mood and anxiety disorders, in their various forms and combinations, constitute a major source of personal suffering and impaired ability to engage in productive work and interpersonal relationships in the United States today. Between five and nine percent of women, and between two and three percent of men meet the diagnostic criteria for major depression at any time; ten to twenty-five percent of all women suffer major depression at some point in their lives, while five to ten percent of men will develop a major depressive disorder (American Psychiatric Association, 1994). Anxiety disorders, e.g., obsessive-compulsive disorder (OCD), post-traumatic stress disorder (PTSD), panic disorder and generalized anxiety disorder (GAD), show lifetime prevalence rates of approximately 2.5%, 7%, 2.5% and 5%, respectively. Between 3% and 13% of individuals in community samples are regarded as meeting the diagnostic criteria for social phobia. Mood and anxiety disorders are common co-morbidities (American Psychiatric Association, 1994), and the most common antidepressant medications, including serotonin re-uptake inhibitors, mixed serotonin-catecholamine re-uptake inhibitors, tricyclic antidepressants, and monoamine oxidase inhibitors—are all effective treatments for anxiety and panic attacks.

Affective disorders, while characterized by depressed mood of varying degrees, exist in various forms. Thus, melancholic depression is characterized by continuously depressed mood and pervasive hopelessness, insomnia with early morning awakening (including the inability to return to sleep), loss of appetite and weight loss, and excessive feelings of guilt (American Psychiatric Association, 1994). In contrast, so-called "atypical" depression is characterized by hypersomnia (over sleeping), hyperphagia, weight gain and, often, mood reactivity. In general, regardless of whether or not the depressive syndrome is melancholic, atypical or some mixture of the two, a diagnosis of major depression is given when depressed mood, or loss of interest or pleasure in all activities, is present for at least two weeks (American Psychiatric Association, 1994). If less severe or incapacitating, depressed mood is considered dysthymia. Depressed mood can occur in the form of a cycling mood abnormality, such as bipolar mood disorder, cyclothymia, or menstrual-related mood disorder. Mood disorders include, for example, depression, major depression, melancholic depression, atypical depression, minor depression, seasonal depression, bipolar affective disorder, dysthymia disorder, menstrual-related dysphoria, chronic fatigue syndrome, depression associated with somatoform disorder, fibromyalgia, and treatment-resistant depression. Commonly seen anxiety disorders include post-traumatic stress disorder, generalized anxiety disorder, panic disorder with and without agoraphobia, social phobia, tics, Tourette's Syndrome, and obsessive-compulsive disorder.

Mood disorders are commonly seen in general medical practice and some general medical disorders resemble depression in important respects. In particular, both fibromyalgia and chronic fatigue syndrome are medical disorders that have clinical and pathophysiologic features in common with atypical depression.

Recently, 1-amino-4-phenyltetralin compounds have become widely used for the treatment of mood and anxiety disorders. See, for example, U.S. Pat. No. 4,029,731, Sarges, issued Jun. 14, 1977; U.S. Pat. No. 4,045,488, Sarges, issued Aug. 30, 1977; U.S. Pat. No. 4,536,518, Welch et al., issued Aug. 20, 1985, and U.S. Pat. No. 4,556,676, Welch et al., issued Dec. 3, 1985, all of which are incorporated herein by reference. An example of such a material is cis-(1S)-N-methyl-4-(3,4-dichlorophenyl)-1,2,3,4-tetrahydro-1-naphthalenamine hydrochloride, also known as sertraline hydrochloride (Zoloft), commercially available from Pfizer, Inc., New York, N.Y., This material is of growing importance as a treatment modality for anxiety and mood disorders.

Although effective pharmaceuticals, including Zoloft, are known for the treatment of mood and anxiety disorders, compliance with treatment regimens (i.e., assuring that the patient take the prescribed medication as scheduled) is a significant issue, particularly with regard to the more serious mood disorders. Some studies suggest that non-compliance rates for antidepressants are between 30% and 60% of the patients being treated. See Markowitz, et al., AIDS, 8: 403–412 (1994); and Demyttenaere, J. Affective Disorders, 43: 27–39 (1997). In particularly serious cases, non-compliance can lead to intensification of the medical condition and even potential injury to the patient or to others. Accordingly, it would be highly desirable to have a dosage form of an effective antidepressant medication, such as sertraline, which provides long-acting efficacy after it is administered. For example, it would be highly desirable to be able to administer the pharmaceutical agent once a month, or even at longer frequencies, rather than relying on the patient to dose themselves once or multiple times each day.

Long lasting (sustained release) treatment modalities for mental disorders have been suggested. For example, U.S. Provisional Patent Application Serial No. 60/183,135, Zemlan, filed February 17, 2000, describes the use of certain long-chain derivatives of compounds such as fluoxetine, particularly fluoxetine decanamide, as single-dose long-lasting drugs for the treatment of depression-related disorders.

U.S. Pat. No. 5,955,459, Bradley, et al., issued Sep. 21, 1999, describes conjugates of fatty acid molecules, such as cis-docosahexaenoic acid, with anti-psychotic agents, such as clozapine. These conjugates are taught to be useful in treating psychotic conditions and are said to provide a longer period of action (a single dose per day, rather than multiple doses per day) when compared to the non-conjugate drug.

U.S. Pat. No. 5,770,231, Mesens, et al., issued Jun. 23, 1998; U.S. Pat. No. 5,650,173, Ramstack, et al., issued Jul. 22, 1997; and U.S. Pat. No. 5,654,008, Herbert, et al., issued Aug. 5, 1997, describe biodegradable and biocompatible microparticles which can be used for the sustained release delivery of a wide range of pharmaceutical materials. Antidepressant materials are not included in the pharmaceutical actives taught to be useful in these patents.

U.S. Pat. Nos. 5,622,657; 5,651,990; 5,723,269; 5,178,878; and 6,022,562 describe various types of microparticles that can be used to deliver pharmaceutically-active agents. Antidepressant materials are mentioned in some of the patents as being useful for delivery using the specifically disclosed microcapsules.

SUMMARY OF THE INVENTION

The present invention relates to pharmaceutically-active materials comprising an antidepressant compound selected from the group consisting of fluoxetine, paroxetine, sertraline, nefazodone, venlafaxine, trazodone, buproprion, mirtazapine, fluvoxamine, duloxetine, pharmaceutically-acceptable salts of those compounds, long-chain derivatives of those compounds, and mixtures thereof, contained in microparticles formulated so as to release the antidepressant compound, when introduced into the patient, over an extended period of time.

Preferred microparticles are produced by dissolving in a solvent the anti-depressant compound and a biodegradable and biocompatible polymer (such as poly(lactic) acid, poly (glycolic acid), copolymers of the foregoing, polyorthoesthers, and mixtures thereof) to form an organic phase, and extracting the solvent to form the microparticles. Preferred antidepressant compounds are sertraline, pharmaceutically-acceptable salts of sertraline, and long-chain derivatives of sertraline, particularly, sertraline hydrochloride and sertraline decanamide.

The present invention also encompasses pharmaceutical compositions comprising a safe and effective amount of the pharmaceutically-active microparticle materials described above, together with a pharmaceutically-acceptable carrier.

Finally, the present invention encompasses a method of treating depression or depression-related conditions comprising administering to a patient in need of such treatment a safe and effective amount of the pharmaceutically-active microparticle materials described above.

All percentages, parts and ratios defined herein are "by weight", unless otherwise specified.

DETAILED DESCRIPTION OF THE INVENTION

The present invention encompasses pharmaceutically-active materials and pharmaceutical compositions, incorporating those active materials, which are effective in the treatment of mood and anxiety disorders, such as depression. The materials and compositions of the present invention are preferably administered by injection, such as subcutaneously or intramuscularly, and provide a long-acting anti-depression benefit. The method of treating depression-related illnesses in humans and animals utilizing these pharmaceutically-active materials and pharmaceutical compositions is also disclosed.

The pharmaceutically-active materials of the present invention comprise a specific group of antidepressant compounds contained in microparticles which act to release the antidepressant compounds, when introduced into a patient, over an extended period of time. As used herein, "extended period of time" is meant to include periods of pharmaceutical activity which are longer than those provided when the same dosage of the same drug is not incorporated into the microparticles described herein. Preferably, "extended period of time" includes periods of from about one week to about one year, preferably from about one week to about six months.

The antidepressant compounds (and their pharmaceutically-acceptable salts) utilized in the present invention are selected from fluoxetine (particularly fluoxetine HCl), paroxetine (particularly paroxetine HCl), sertraline (particularly sertraline HCl), nefazodone (particularly nefazodone (HCl), venlafaxine (particularly venlafaxine (HCl), buproprion (particularly buproprion HCl), duloxetine (particularly duloxetine HCl), and mirtzapine. Mixtures of these materials may also be used. Pharmaceutically-acceptable salts, in addition to the hydrochloride salt, may also be used. These materials are very well-known to those skilled in the art, and are described, for example, in the Merck Index and in the Physician's Desk Reference.

In addition to the compounds themselves, the microparticles of the present invention may include covalent conjugates of $C_6$–$C_{26}$ fatty acids with the anti-depressant compounds. Fatty acids are also well-known to those skilled in the art. They may be derived from natural sources, such as fish oils, or synthesized. Preferred fatty acids are the unbranched common naturally-occurring fatty acids. Examples of such acids includes lauric acid, myristic acid, palmitic acid, palmitoleic acid, stearic acid, oleic acid, vaccenic acid, linoleic acid, arachidonic acid, and docosahexaenoic acid. Highly preferred unbranched fatty acids are those containing 6 to 12 carbon atoms, particularly those with 8 carbon atoms.

Preferred long-chain derivatives of the antidepressant compounds are those having the formula:

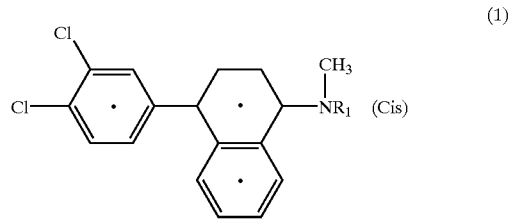

(1)

and the pharmaceutically-acceptable acid addition salts thereof, wherein:

$R_1$ is selected from substituted and unsubstituted moieties, including

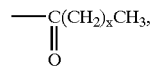

$C_6$–$C_{20}$ alkyl, and $C_6$–$C_{20}$ alkenyl;

wherein x is from about 6 to about 20, with 8 being preferred.

The term "Cis" refers to the relative orientation of the $NR_1CH_3$ and 3,4-dichlorophenyl moieties on the cyclohexane ring (i.e., they are both oriented on the same side of the ring). Because both the 1- and 4-carbons of formula (1) are asymmetrically substituted, each cis-compound has two optically active enantiomeric forms denoted (with reference to the 1 carbon) as the cis(1R) and the Cis (1S) enantiomers. The preferred embodiment is the enantiomer cis-(1S)-N-methyl-4-(3,4-dichlorophenyl)-1,2,3,4-tetrahydro-1-naphthalenamine and its pharmaceutically acceptable acid addition salts.

A particularly preferred antidepressant compound of this type is sertraline decanamide, having the following formula:

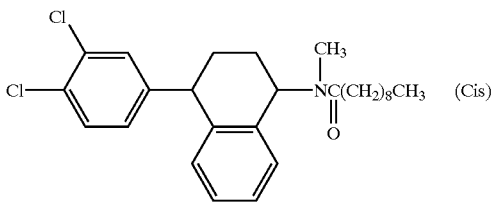

Preferred antidepressant materials for use in the present invention include sertraline and its pharmaceutically-acceptable salts, particularly sertraline hydrochloride, as well as the long-chain derivatives of sertraline, particularly sertraline decanamide.

Any method known in the art for forming biocompatible sustained-release microparticles may be used for preparing the present invention. The preferred method for forming the microparticles of the present invention is disclosed in U.S. Pat. No. 5,770,231, Meszens, et al., issued Jun. 23, 1998, incorporated herein by reference.

By the term "administered", as used herein, is intended to include any method of delivering the antidepressant active-containing microparticles of the invention to a warm-blooded animal, such as, for example, parenteral (intravenous, intramuscular or subcutaneous) administration. By "microparticles", as used herein, is meant solid particles that contain one or more of the defined antidepressant pharmaceutical actives, either in solution or in crystalline form, having a particle size of from about 25 to about 180 microns. Crystalline form is preferred. The active agent is dispersed or dissolved within the polymer that serves as the matrix of the microparticle.

The product of the present invention offers the advantage of duration of action ranging from about one week (7 days) to about one year, depending upon the type of microparticle selected. In a preferred embodiment, the microparticles are designed to afford treatment to patients over a period of from about 30 to about 60 days. The duration of action can be controlled by manipulation of the polymer composition, polymer:drug ratio, microparticle wall structure and thickness, and microparticle size.

The polymeric matrix material used to make the microparticles of the present invention is a biocompatible and biodegradable polymeric material. The term "biocompatible" is defined as a polymeric material that is not toxic to the human body, is not carcinogenic, and does not cause significant inflammation in body tissues. The matrix material should be biodegradable in the sense that the polymeric material should degrade by bodily processes into products which are readily disposable by the body and should not accumulate in the body. The products of the biodegradation should also be biocompatible with the body in the same sense that the polymeric matrix is biocompatible with the body. Suitable examples of polymeric matrix materials include poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein and waxes, such as glycerol mono- and di-stearate, and the like. The preferred polymer for use in the practice of this invention is poly(D,L-lactide-co-glycolide). It is preferred that the molar ratio of lactide to glycolide in such a copolymer be in the range of from about 85:15 to about 50:50.

In a preferred embodiment, administration of the antidepressant materials to patients by the method of the present invention is achieved by a single administration of the drug-loaded microparticles, releasing the drug in a constant or pulsed manner over time into the patient and eliminating the need for repetitive doses.

The materials of the present invention contain an antidepressant pharmaceutical active dispersed in a microparticle matrix material. The amount of pharmaceutical agent incorporated in the microparticles usually ranges from about 1% to about 90%, preferably from about 30% to about 50%, more preferably from about 35% to about 40%. In these formulations, percent is intended to mean weight parts of pharmaceutical agent per total weight of microparticle. For example, 10% agent would mean 10 parts pharmaceutical agent and 90 parts polymer by weight.

The molecular weight of the polymeric matrix material is of some importance. The molecular weight should be high enough to permit the formation of satisfactory polymer coatings, i.e., the polymer should be a good film former. Usually, a satisfactory molecular weight is in the range of from about 5,000 to about 500,000 daltons, preferably about 150,000 daltons. However, since the properties of the film are also partially dependent on the particular polymeric material being used, it is very difficult to specify an appropriate molecular weight range for all polymers. The molecular weight of a polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials, a microparticle formulation can be made in which the resulting microparticles exhibit both diffusional release and biodegradation release properties. This is useful in affording multiphasic release patterns.

The microparticle product of the present invention can be prepared by any method capable of producing microparticles in a size range acceptable for use in an injectable composition. Preferred methods of preparation are those described in U.S. Pat. Nos. 4,389,330, and 5,770,231, both of which are incorporated herein by reference. In these methods, the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle can be blended in the solvent medium together.

Solvents for the agent and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as benzyl alcohol; ethyl acetates; and the like. A preferred solvent for use in the practice of the present invention is a mixture of benzyl alcohol and ethyl acetate.

The mixture of ingredients in the solvent is emulsified in a continuous phase processing medium, the continuous phase medium being such that a dispersion of microparticles containing the indicated ingredients is formed in the continuous phase medium. The continuous phase processing medium and the organic phase must be largely immiscible. The continuous phase processing medium most commonly employed is water, although non-aqueous media, such a xylene, toluene, and synthetic and natural oil can also be used. Usually a surfactant is added to the continuous phase processing medium to prevent the microparticles from agglomerating and to control the size of the solvent microdroplets in the emulsion. A preferred surfactant-dispersing medium combination is a 0.1–10%, more preferably 0.5–2%, solution of poly(vinyl alcohol) in water. The dispersion is formed by mechanical agitation of the mixed materials. An emulsion can also be formed by adding small drops of active agent-matrix material solution to the continuous phase processing medium. The temperature during the formation of the emulsion is not especially critical, but can influence the size and quality of the microparticles and the solubility of the agent in the continuous phase. Of course, it is desirable to have as little of the pharmaceutical agent in the continuous phase as possible. Moreover, depending on the solvent and the continuous phase processing medium employed, the temperature must not be too low or the solvent and processing medium will solidify or become too viscous for practical purposes. On the other hand, it must not be so high that the processing medium will evaporate or that the liquid processing medium will not be maintained. Moreover, the temperature of the medium cannot be so high that the stability of the particular pharmaceutical active agent being incorporated in the microparticles is adversely affected. Accordingly, the dispersion process should be conducted at any temperature that maintains stable operating conditions, preferably from about 20° C. to about 60° C., depending upon the pharmaceutical agent and excipient utilized.

The dispersion formed is stable and from this dispersion the organic phase fluid can be partially removed in the first step of the solvent removal process. The solvent can easily be removed by common techniques, such as heating, the application of a reduced pressure, or the combination of both. The temperature employed to evaporate solvent from the microdroplets is not critical, but should not be so high as to degrade the pharmaceutical agent employed in the preparation of a given microparticle or to evaporate solvent at a rate rapid enough to cause defects in the wall-forming material. Generally, from about 10% to about 90%, preferably from about 40% to about 60%, of the solvent is removed in the first solvent removal step.

After the first stage, the dispersed microparticles in the solvent-miscible fluid medium are isolated from the fluid medium by any convenient means of separation. Thus, for example, the fluid can be decanted from the microparticles or the microparticle suspension can be filtered. Various other combinations of separation techniques can be used, if desired.

Following the isolation of the microparticles from the continuous phase processing medium, the remainder of the solvent in the microparticles is removed by extraction. In this step, the microparticles can be suspended in the same continuous phase processing medium used in the first step, with or without surfactant, or in another liquid. The extraction medium removes the solvent from the microparticles, but does not dissolve them. During the extraction, the extraction medium containing dissolved solvent must be removed and replaced with fresh extraction medium. This is best done on a continual or continuous basis where the rate of extraction medium replenishment is critical. If the rate is too slow, crystals of the pharmaceutical agent may protrude from the microparticles or grow in the extraction medium. Obviously, the rate of extraction medium replenishment for a given process is a variable that can easily be determined at the time the process is performed and, therefore, no precise limits for this rate need be predetermined. After the remainder of the solvent has been removed, the microparticles are dried by exposure to air or other conventional drying techniques, such as vacuum drying, drying over a desiccant, or the like. This process is very efficient in encapsulating the pharmaceutically-active agent since core loadings of up to about 80%, preferably up to about 50%, can be obtained.

Another preferred method of encapsulating the specifically-defined anti-depressant compounds to form the controlled-released microparticles of the present invention includes the use of static mixers, as described in U.S. Pat. No. 5,654,008, Herbert, et al., issued Aug. 5, 1997, incorporated herein by reference.

The pharmaceutical compositions of the present invention comprise:

(a) a safe and effective amount of the antidepressant compound-containing microparticle materials, as described above; and (b) a pharmaceutically-acceptable vehicle.

As used herein, the phrase "a safe and effective amount", when used in conjunction with the pharmaceutical active-containing microparticles described herein, is meant to denote an amount sufficient to provide an effective antidepressant or anti-anxiety benefit to the patient, taking into consideration the age, size, physical condition and medical condition of the patient, and the release rate of the microparticles for the active agent, without being so great as to cause undue side effects, within the sound medical judgment of the treating physician.

Preferred compositions of the present invention contain from about 5% to about 50%, preferably from about 20% to about 45%, of the pharmaceutical active containing microparticles, and from about 50% to about 95%, preferably from about 55% to about 80% of the pharmaceutically-acceptable vehicle.

As used herein, the term "pharmaceutically-acceptable vehicle" denotes a solid or liquid filler, or diluent used in combination with the antidepressant pharmaceutical active containing microcapsules to form a pharmaceutical composition which is easy to formulate and easy to administer. These vehicles must be biocompatible, as that term is described herein. Some examples of substances that can serve as pharmaceutically-acceptable vehicles include sugars, such as lactose, glucose and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid, magnesium stearate; calcium sulfate; vegetable oils, such as peanut oil, cottonseed oil, sesame oil, olive oil, corn oil, and oil of theobroma; polyols, such as propylene glycol, glycerin, sorbitol, mannitol, and polyethylene glycol; agar; alginic acid; pyrogen-free water; isotonic saline; and phosphate buffer solutions, as well as other non-toxic compatible substances conventionally used in pharmaceutical compositions. Wetting agents and lubricants, such as sodium lauryl sulfate, as well as coloring agents, flavoring agents, tableting agents, dissolution agents, stabilizers and preservatives, can also be present in the compositions. Formulation is done using conventional pharmaceutical formulational techniques. The pharmaceutical carriers employed in the compositions of the present invention are used at concentrations to provide a practical size to dosage relationship for the composition.

Preferred vehicles for use in the compositions of the present invention are liquid vehicles which are suited for injectable delivery such as a solution of carboxymethyl cellulose. Other preferred vehicles include lipid or oil-based vehicles. These oil-based vehicles include plant and animal oils and fats consisting of the mono-, di- and tri-glycerides of various fatty acids or containing these as main constituents; fatty acid esters of alcohols; higher aliphatic alcohols; saturated or unsaturated fatty acids; the commercially-available synthetic and semi-synthetic mono-, di- and triglyceride oils and glycerol ethers; certain types of wax and mixtures of two or more of the above-described substances. The oil-based vehicles are preferably liquid at typical usage and storage temperatures (i.e., temperatures of from about 10° C. to about 30° C.). Preferred oil-based vehicles include vegetable oils, such as peanut oil, cottonseed oil, sesame oil, olive oil, corn oil, and oil of theobroma; with sesame oil being particularly preferred.

The present invention also encompasses a method for treating mood and anxiety disorders in humans and animals in need of such treatment. In this method, a safe and effective amount of the pharmaceutical active-containing microparticles, as defined above, is administered to the patient. It is preferred that the microparticles be administered as a part of pharmaceutical composition, as described above. The conditions which may be treated using the method of the present invention include any mood or anxiety disorders, including, for example, depression, major depression, melancolic depression, atypical depression, minor depression, seasonal depression, bi-polar affective disorder, dysthymia, menstrual-related dysforia, chronic fatigue syndrome, depression associated with somatiform disorder, fibromyalgia, treatment-resistant depression, traumatic stress disorder, generalized anxiety disorder, panic disorder with or without agorophobia, social phobia, tics, Tourrette's Syndrome, and obsessive-compulsive disorder. The method is particularly useful for the treatment of depression, depression-related conditions, and anxiety disorders.

It is particularly preferred that the compositions of the present invention be administered by injection, such as subcutaneously, intramuscularly or intraperitoneally. When administered in this way, the compositions provide a "depot effect", yielding a long-acting antidepressant benefit to the patient. Specifically, antidepressant active is released at a controlled rate over an extended period of time from the microparticles to the patient. This allows a single dose of the active to be administered per week, per month, or per several months, rather than requiring one or several doses per day.

In the method of the present invention, the antidepressant pharmaceutically-active compound is administered in a safe and effective amount, particularly from about 25 to about 110 mg per day. When administered as depot treatment, by injection, the typical amount of pharmaceutically-active compound administered is from about 150 to about 750 mg per month. Such a dosage can provide an effective antidepressant effect for up to several weeks or a month, or more, depending on the concentration of the pharmaceutically-active compound and the release characteristics of the microcapsules.

EXAMPLE

Preparation Of 40% Loaded Sertraline Microparticles

First the aqueous phase (solution A) is prepared by weighing and mixing 904.4 g 1% poly (vinyl alcohol) (Vinyl 205, Air Products and Chemical Inc., Allentown, Pa.), 30.1 g benzyl alcohol (J. T. Baker, Phillipsburg, N.J.) and 65.8 g ethyl acetate (Fisher Scientific, Fair Lawn, N.J.). Then the organic phase (solution B) is prepared by dissolving 27.1 g of high viscosity 75:25 dl (polylactide-coglycolide) (Medisorb Technologies International, L.P., Cincinnati, Ohio.) in 99.3 g ethyl acetate and 99.1 g benzyl alcohol. Once the polymer is completely dissolved, 18.1 g sertraline base is added and dissolved in the polymer solution. The exposure time of the dissolved sertraline with the polymer is kept to a minimum (<10 minutes). Solutions A and B are then pumped through a ¼inch diameter static mixer (Cole Parmer L04667-14) via a gear drive pump and head (Cole Parmer L07149-04, L070P2-16) at flow rates of 198 and 24 ml/minute, respectively, and into a quench composed of 55 liters of water for injection containing 1375.6 g of ethyl acetate, 924.4 (0.02 Molar) of anhydrous sodium bicarbonate, and 116.6 g (0.02 Molar) of anhydrous sodium carbonate (Mallinckrodt Specialty Chemicals, Paris, Ky.) at 12° C. The microparticles are allowed to stir in the first wash for 2 hours, then isolated by sieving with a 25-micron sieve. The product retained by the sieve is transferred to a 20-liter wash at 12° C. After stirring in the sieved wash for 3 hours, the microparticles are isolated and size fractionated by sieving through a stainless-steel sieve column composed of 25- and 180-micron sizes. The microparticles are dried overnight, then collected and weighed.

The microparticles are then lyophilized. The microparticles are weighed in 5 cc serum vials. Then an aqueous vehicle composed of 0.75% CMC, 5% Mannitol, and 0.1% Tween 20 is added to the vials. The microparticles are suspended in the vehicle by agitation, then quickly frozen in a dry ice/acetone bath. The vials are then lyophilyzed in a pilot scale lyophilizer (Dura Stop Microporcessor Control, FTS Systems, Inc., Stone Ridge, N.Y.) employing a ramped 30° C. maximum temperature cycle for 50 hours. The lyophilyzed microparticles may be subsequently sterilized by 2.2 Mrad gamma irradiation from a $^{60}$Co source. The lyophilyzed microparticles are reconstituted in sterile water for injection immediately prior to injection. The appropriate volume of the respective depot formulation required to deliver a therapeutically effective antidepressant dose, typically 150 to about 750 mg, is administered to a patient via intramuscular injection.

What is claimed is:

1. A pharmaceutically-active material consisting essentially of an antidepressant compound selected from the group consisting of sertraline, pharmaceutically-acceptable salts of sertraline, long chain derivatives of sertraline, and mixtures thereof, contained in microparticles formulated so as to release the antidepressant compound, when introduced into a patient, over an extended period of time.

2. The pharmaceutically-active material according to claim 1 wherein the microparticles are formulated so as to release the antidepressant compound over a period of from about one week to about one year.

3. The pharmaceutically-active material according to claim 1 wherein the long-chain sertraline derivatives have the formula:

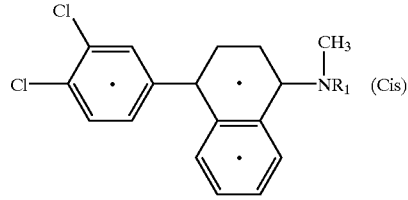

wherein $R_1$ is selected from substituted and unsubstituted moieties selected from

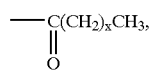

$C_6$–$C_{20}$ alkenyl, and $C_6$–$C_{20}$ alkenyl, wherein x is from about 6 to about 20; and pharmaceutically-acceptable salts thereof.

4. The pharmaceutically-active material according to claim 3 wherein antidepressant compound is sertraline decanamide.

5. The pharmaceutically-active material according to claim 1 wherein the microparticles contain from about 1% to about 90% of the antidepressant compound.

6. The pharmaceutically-active material according to claim 5 wherein the antidepressant compound is present in the microparticles in crystalline form.

7. The pharmaceutically-active material according to claim 6 wherein the microparticles have a size of from about 25 to about 180 microns.

8. The pharmaceutically-active material according to claim 7 wherein the microparticles are produced by dissolving in a solvent the antidepressant compound and a biodegradable and biocompatible polymer to form an organic phase, and extracting the solvent to form microparticles.

9. The pharmaceutically-active material according to claim 8 wherein the polymer is selected from the group consisting of poly(lactic) acid, poly(glycolic) acid, copolymers of the foregoing, poly(aliphatic carboxylic acid), copolyoxalates, polycaprolactone, polydioxonene, poly(ortho carbonates), poly(acetals), poly(lactic acid-caprolactone), poly(orthoethers), poly(glycolic acid-caprolactone), polyanhydrides, albumin, casein, waxes, and mixtures thereof.

10. The pharmaceutically-active material according to claim 9 wherein the polymer is selected from the group consisting of poly(lactic) acid, poly(glycolic) acid, copolymers of the foregoing, poly(ortho esters), and mixtures thereof.

11. A pharmaceutical composition comprising:
(a) a safe and effective amount of the pharmaceutically-active material according to claim 1; and
(b) a pharmaceutically-acceptable carrier.

12. A pharmaceutical composition comprising:
(a) a safe and effective amount of the pharmaceutically-active material according to claim 10; and
(b) a pharmaceutically-acceptable carrier.

13. A method of treating depression or depression-relating conditions comprising administering to a patient in need of such treatment a safe and effective amount of a pharmaceutically-active material according to claim 1.

14. A method of treating depression or depression-related conditions comprising administering to a patient in need of such treatment a safe and effective amount of the pharmaceutically-active material according to claim 10.

15. A method of achieving in a patient a therapeutic effect longer than that achieved when an equimolar amount of an antidepressant agent is administered comprising administering to that patient a safe and effective amount of the pharmaceutically-active material according to claim 1.

16. A method of achieving in a patient a therapeutic effect longer than that achieved when or equimolor amount of an antidepressant agent is administered comprising administering to that patient a safe and effective amount of the pharmaceutically-active material according to claim 10.

17. A pharmaceutically-active material consisting essentially of an anti-depressant compound selected from the group consisting of fluoxetine, paroxetine, sertraline, nefazodone, venlafaxine, trazodone, mirtazapine, fluvoxamine, pharmaceutically-acceptable salts of those compounds, long-chain derivatives of those compounds, and mixtures thereof, contained in microparticles formulated so as to release the anti-depressant compound, when introduced into a patient, over an extended period of time.

* * * * *

UNITED STATES PATENT AND TRADEMARK OFFICE
CERTIFICATE OF CORRECTION

PATENT NO.    : 6,482,440 B2
DATED         : November 19, 2002
INVENTOR(S)   : Zemlan et al.

It is certified that error appears in the above-identified patent and that said Letters Patent is hereby corrected as shown below:

<u>Column 11,</u>
Line 5, the first occurrence of "alkenyl" should read -- alkyl --

Signed and Sealed this

Eighth Day of April, 2003

JAMES E. ROGAN
*Director of the United States Patent and Trademark Office*